United States Patent [19]
Tompkins et al.

[11] Patent Number: 5,413,927
[45] Date of Patent: May 9, 1995

[54] FELINE IMMUNODEFICIENCY VIRUS ISOLATE NCSU₁

[75] Inventors: Wayne A. F. Tompkins; Mary B. Tompkins, both of Apex, N.C.

[73] Assignee: North Carolina State University, Raleigh, N.C.

[21] Appl. No.: 105,710

[22] Filed: Aug. 12, 1993

Related U.S. Application Data

[63] Continuation-in-part of Ser. No. 752,424, Sep. 3, 1991, abandoned.

[51] Int. Cl.⁶ .......................... C12N 5/06; C12N 7/00; C12N 7/02; C12N 15/49
[52] U.S. Cl. ............................... 435/239; 435/235.1; 435/240.2; 435/948
[58] Field of Search .................... 435/235.1, 239, 240.2

[56] References Cited

U.S. PATENT DOCUMENTS 5,037,753  8/1991  Pedersen et al. ................ 435/235.1
5,275,813  1/1994  Yamamoto et al. ................ 424/89

FOREIGN PATENT DOCUMENTS

WO90/13573 of 1990 WIPO .

OTHER PUBLICATIONS

T. Miyazawa et al. (1989) Archives of Virology 108: 59–68.

T. R. Phillips et al. (1990) Journal of Virology 64(10): 4605–4613.

E. Verschoor et al. (1990) J. Cell Biochem. Suppl. 14D: p. 143, Abstract L340.

N. Maki et al., *Molecular characterization and heterogeneity of feline immunodeficiency virus isolates* Arch Virol 123: 29–45 (1992).

Shigeru Morikawa et al., *Analyses of the Requirements for the Synthesis of Virus–like Particles by FEline Immunodeficiency Virus gag Using Baculovirus Vectors* Virology 183: 288–297 (1991).

N. C. Pedersen et al., *Feline Leukemia Virus Infection as a Potentiating Cofactor for the Primary and Secondary Stages of Experimentally Induced Feline Immunodeficiency Virus Infection* Journal of Virology 64: 598–606 (1990).

R. A. Olmsted et al., *Nucleotide sequence of feline immunodeficiency virus: Genome organization and relationship to other lentiviruses* Proc. Natl. Acad. Sci. 86: 8088–8092 (1989).

R. A. Olmsted et al., *Molecular cloning of feline immunodeficiency virus* Proc. Natl. Acad. Sci. 86: 2448–2452 (1989).

R. L. Talbott et al., *Nucleotide sequence and genomic organization of feline immunodeficency virus* Proc. Natl. Acad. Sci. 86: 5743–4747 (1989).

Primary Examiner—Jacqueline Stone
Assistant Examiner—Johnny F. Railey, II
Attorney, Agent, or Firm—Bell, Seltzer, Park & Gibson

[57] ABSTRACT

Disclosed is an isolated and purified feline immunodeficiency virus (FIV) culture having the identifying characteristics of FIV isolate NCSU₁. A biologically pure culture of host cells containing a FIV having the identifying characteristics of FIV isolate NCSU₁ is also disclosed, along with isolated and purified DNA coding for (a) an FIV having the identifying characteristics of FIV isolate NCSU₁, or (b) an antigenic fragment of an FIV having the identifying characteristics of FIV isolate NCSU₁. Various vaccine formulations containing active agents derived from the foregoing FIV virus, DNA encoding the virus, and DNA encoding antigenic fragments of the virus are also disclosed herein.

Also disclosed are immunodeficient mice containing feline tissue, which feline tissue is capable of infection with a feline immunodeficiency virus such as (but not limited to) FIV isolate NCSU₁.

2 Claims, 5 Drawing Sheets

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

GGATGAGTAT TGGAACCCTG AA 22

( 2 ) INFORMATION FOR SEQ ID NO:2:

( i ) SEQUENCE CHARACTERISTICS:

(A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:2:

GATTCCGAGA CCTCACAGGT AA                                                                     22

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

GGACTTTTGA GTTCTCCCTT                                                                        20

(2) INFORMATION FOR SEQ ID NO:4:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

CTCTCTGAGA TGTCGTTGTA CC                                                                     22

(2) INFORMATION FOR SEQ ID NO:5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

TCTGGCCTCA TTTCTAATGA TG                                                                     22

(2) INFORMATION FOR SEQ ID NO:6:

(i) SEQUENCE CHARACTERISTICS:
        (A) LENGTH: 1418 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 23..1372

(xi) SEQUENCE DESCRIPTION: SEQ ID NO:6:

```
GTAGGAGAGA TTCTACAGCA AC ATG GGG AAT GGA CAG GGG CGA GAT TGG AAA          52
                         Met Gly Asn Gly Gln Gly Arg Asp Trp Lys
                          1               5                  10

ATG GCC ATT AAG AGA TGT AGT AAT GCT GCT GTA GGA GTA GGG GGG AAG          100
Met Ala Ile Lys Arg Cys Ser Asn Ala Ala Val Gly Val Gly Gly Lys
         15                  20                  25
```

| | | | | | | | | | | | | | | | | |
|---|---|---|---|---|---|---|---|---|---|---|---|---|---|---|---|---|
| AGT | AAA | AAA | TTT | GGG | GAA | GGG | AAT | TTC | AGA | TGG | GCC | ATT | AGA | ATG | GCT | 148 |
| Ser | Lys | Lys | Phe 30 | Gly | Glu | Gly | Asn | Phe 35 | Arg | Trp | Ala | Ile | Arg 40 | Met | Ala | |
| AAT | GTA | TCT | ACA | GGA | CGA | GAA | CCT | GGT | GAT | ATA | CCA | GAG | ACT | TTA | GAT | 196 |
| Asn | Val | Ser 45 | Thr | Gly | Arg | Glu | Pro 50 | Gly | Asp | Ile | Pro | Glu 55 | Thr | Leu | Asp | |
| CAA | CTA | AGG | TTG | GTT | ATT | TGC | GAT | TTA | CAA | GAA | AGA | AGA | AAA | AAA | TTT | 244 |
| Gln | Leu 60 | Arg | Leu | Val | Ile | Cys 65 | Asp | Leu | Gln | Glu | Arg 70 | Arg | Lys | Lys | Phe | |
| GGA | TCT | TGC | AAA | GAA | ATT | GAT | AAG | GCA | ATT | GTT | ACA | TTA | AAA | GTC | TTT | 292 |
| Gly 75 | Ser | Cys | Lys | Glu | Ile 80 | Asp | Lys | Ala | Ile | Val 85 | Thr | Leu | Lys | Val | Phe 90 | |
| GCG | GCA | GTA | GGA | CTT | TTA | AAT | ATG | ACA | GTG | TCT | TCT | GCT | GCT | GCA | GCT | 340 |
| Ala | Ala | Val | Gly | Leu 95 | Leu | Asn | Met | Thr | Val 100 | Ser | Ser | Ala | Ala 105 | Ala | Ala | |
| GAA | AAT | ATG | TTC | ACT | CAG | ATG | GGA | TTA | GAC | ACT | AGA | CCA | TCT | ATG | AAA | 388 |
| Glu | Asn | Met | Phe 110 | Thr | Gln | Met | Gly | Leu 115 | Asp | Thr | Arg | Pro | Ser 120 | Met | Lys | |
| GAA | GCA | GGA | GGA | AAA | GAG | GAA | GGC | CCT | CCA | CAG | GCA | TTT | CCT | ATT | CAA | 436 |
| Glu | Ala | Gly 125 | Gly | Lys | Glu | Glu | Gly 130 | Pro | Pro | Gln | Ala | Phe 135 | Pro | Ile | Gln | |
| ACA | GTA | AAT | GGA | GTA | CCA | CAA | TAT | GTA | GCA | CTT | GAC | CCA | AAA | ATG | GTG | 484 |
| Thr | Val | Asn 140 | Gly | Val | Pro | Gln | Tyr 145 | Val | Ala | Leu | Asp | Pro 150 | Lys | Met | Val | |
| TCC | ATT | TTT | ATG | GAA | AAG | GCA | AGA | GAA | GGA | TTA | GGA | GGT | GAG | GAA | GTT | 532 |
| Ser 155 | Ile | Phe | Met | Glu | Lys 160 | Ala | Arg | Glu | Gly | Leu 165 | Gly | Gly | Glu | Glu | Val 170 | |
| CAG | CTA | TGG | TTC | ACT | GCC | TTC | TCT | GCA | AAT | TTA | ACA | CCT | ACT | GAC | ATG | 580 |
| Gln | Leu | Trp | Phe | Thr 175 | Ala | Phe | Ser | Ala | Asn 180 | Leu | Thr | Pro | Thr | Asp 185 | Met | |
| GCC | ACA | TTA | ATA | ATG | GCC | GCA | CCA | GGG | TGC | GCT | GCA | GAT | AAA | GAA | ATA | 628 |
| Ala | Thr | Leu | Ile 190 | Met | Ala | Ala | Pro | Gly 195 | Cys | Ala | Ala | Asp | Lys 200 | Glu | Ile | |
| TTG | GAT | GAA | AGC | TTA | AAG | CAA | CTT | ACT | GCA | GGA | TAT | GAT | CGT | ACA | CAT | 676 |
| Leu | Asp | Glu 205 | Ser | Leu | Lys | Gln | Leu 210 | Thr | Ala | Gly | Tyr | Asp 215 | Arg | Thr | His | |
| CCC | CCT | GAT | GCT | CCC | AGA | CCA | TTA | CCC | TAT | TTT | ACT | GCA | GCA | GAA | ATT | 724 |
| Pro | Pro 220 | Asp | Ala | Pro | Arg | Pro 225 | Leu | Pro | Tyr | Phe | Thr 230 | Ala | Ala | Glu | Ile | |
| ATG | GGT | ATT | GGA | TTT | ACT | CAA | GAA | CAA | CAA | GCA | GAA | GCA | AGA | TTT | GCA | 772 |
| Met 235 | Gly | Ile | Gly | Phe | Thr 240 | Gln | Glu | Gln | Gln | Ala 245 | Glu | Ala | Arg | Phe | Ala 250 | |
| CCA | GCT | AGG | ATG | CAG | TGT | AGA | GCA | TGG | TAT | CTC | GAG | GGA | CTA | GGA | AAA | 820 |
| Pro | Ala | Arg | Met | Gln 255 | Cys | Arg | Ala | Trp | Tyr 260 | Leu | Glu | Gly | Leu | Gly 265 | Lys | |
| TTG | GGC | GCC | ATA | AAA | GCT | AAG | TCT | CCT | CGA | GCT | GTG | CAG | TTA | AGA | CAA | 868 |
| Leu | Gly | Ala | Ile 270 | Lys | Ala | Lys | Ser | Pro 275 | Arg | Ala | Val | Gln | Leu 280 | Arg | Gln | |
| GGA | GCT | AAG | GAA | GAT | TAT | TCA | TCC | TTT | ATT | GAC | AGA | TTG | TTT | GCC | CAA | 916 |
| Gly | Ala | Lys 285 | Glu | Asp | Tyr | Ser | Ser 290 | Phe | Ile | Asp | Arg | Leu 295 | Phe | Ala | Gln | |
| ATA | GAT | CAA | GAA | CAA | AAT | ACA | GCT | GAA | GTT | AAG | TTA | TAT | TTA | AAA | CAG | 964 |
| Ile | Asp 300 | Gln | Glu | Gln | Asn | Thr 305 | Ala | Glu | Val | Lys | Leu 310 | Tyr | Leu | Lys | Gln | |
| TCA | TTA | AGC | ATG | GCT | AAT | GCT | AAT | GCA | GAA | TGT | AAA | AAG | CCA | ATG | ACC | 1012 |
| Ser 315 | Leu | Ser | Met | Ala | Asn 320 | Ala | Asn | Ala | Glu | Cys 325 | Lys | Lys | Pro | Met | Thr 330 | |
| CAC | CTT | AAG | CCA | GAA | AGT | ACC | CTA | GAA | GAA | AAG | TTG | AGA | GCT | TGT | CAA | 1060 |
| His | Leu | Lys | Pro | Glu 335 | Ser | Thr | Leu | Glu | Glu 340 | Lys | Leu | Arg | Ala | Cys 345 | Gln | |
| GAA | ATA | GGC | TCA | CCA | GGA | TAT | AAA | ATG | CAA | CTC | TTG | GCA | GAA | GCT | CTT | 1108 |
| Glu | Ile | Gly | Ser | Pro | Gly | Tyr | Lys | Met | Gln | Leu | Leu | Ala | Glu | Ala | Leu | |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     |     |     | 350 |     |     |     |     | 355 |     |     |     |     | 360 |      |
| ACA | AAA | GTT | CAA | GTA | GTG | CAA | TCA | AAA | GGA | TCA | GGA | CCA | GTG | TGT | TTT | 1156 |
| Thr | Lys | Val | Gln | Val | Val | Gln | Ser | Lys | Gly | Ser | Gly | Pro | Val | Cys | Phe |      |
|     |     | 365 |     |     |     |     | 370 |     |     |     |     | 375 |     |     |     |      |
| AAT | TGT | AAA | AAA | CCA | GGA | CAT | CTA | GCA | AGA | CAA | TGT | AGA | GAA | GTG | AGA | 1204 |
| Asn | Cys | Lys | Lys | Pro | Gly | His | Leu | Ala | Arg | Gln | Cys | Arg | Glu | Val | Arg |      |
|     |     | 380 |     |     |     |     | 385 |     |     |     |     | 390 |     |     |     |      |
| AAA | TGT | AAT | AAA | TGT | GGA | AAA | CCT | GGT | CAT | GTA | GCT | GCC | AAA | TGT | TGG | 1252 |
| Lys | Cys | Asn | Lys | Cys | Gly | Lys | Pro | Gly | His | Val | Ala | Ala | Lys | Cys | Trp |      |
| 395 |     |     |     |     | 400 |     |     |     |     | 405 |     |     |     |     | 410 |      |
| CAA | GGA | AAT | AGA | AAG | AAT | TCG | GGA | AAC | TGG | AAG | GCG | GGG | CGA | GCT | GCA | 1300 |
| Gln | Gly | Asn | Arg | Lys | Asn | Ser | Gly | Asn | Trp | Lys | Ala | Gly | Arg | Ala | Ala |      |
|     |     |     |     | 415 |     |     |     |     | 420 |     |     |     |     | 425 |     |      |
| GCC | CCA | GTG | AAT | CAA | GTG | CAG | CAA | GCA | GTA | ATG | CCA | TCT | GCA | CCT | CCA | 1348 |
| Ala | Pro | Val | Asn | Gln | Val | Gln | Gln | Ala | Val | Met | Pro | Ser | Ala | Pro | Pro |      |
|     |     |     | 430 |     |     |     |     | 435 |     |     |     |     | 440 |     |     |      |
| ATG | GAG | GAG | AAA | CTA | TTG | GAT | TTA | TAAATTATAA | TAGAGTAGGT | ACTACTACAA |     |     |     |     |     | 1402 |
| Met | Glu | Glu | Lys | Leu | Leu | Asp | Leu |     |     |     |     |     |     |     |     |      |
|     |     | 445 |     |     |     |     | 450 |     |     |     |     |     |     |     |     |      |
| CATTAGAAAA | GAGGCC |     |     |     |     |     |     |     |     |     |     |     |     |     |     | 1418 |

( 2 ) INFORMATION FOR SEQ ID NO:7:

( i ) SEQUENCE CHARACTERISTICS:
        ( A ) LENGTH: 450 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

| Met | Gly | Asn | Gly | Gln | Gly | Arg | Asp | Trp | Lys | Met | Ala | Ile | Lys | Arg | Cys |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Ser | Asn | Ala | Ala | Val | Gly | Val | Gly | Lys | Ser | Lys | Lys | Phe | Gly | Glu |     |
|     |     |     | 20  |     |     |     |     | 25  |     |     |     | 30  |     |     |     |
| Gly | Asn | Phe | Arg | Trp | Ala | Ile | Arg | Met | Ala | Asn | Val | Ser | Thr | Gly | Arg |
|     |     |     | 35  |     |     |     | 40  |     |     |     |     | 45  |     |     |     |
| Glu | Pro | Gly | Asp | Ile | Pro | Glu | Thr | Leu | Asp | Gln | Leu | Arg | Leu | Val | Ile |
|     |     | 50  |     |     |     |     | 55  |     |     |     |     | 60  |     |     |     |
| Cys | Asp | Leu | Gln | Glu | Arg | Arg | Lys | Lys | Phe | Gly | Ser | Cys | Lys | Glu | Ile |
| 65  |     |     |     |     | 70  |     |     |     |     | 75  |     |     |     |     | 80  |
| Asp | Lys | Ala | Ile | Val | Thr | Leu | Lys | Val | Phe | Ala | Ala | Val | Gly | Leu | Leu |
|     |     |     |     | 85  |     |     |     |     | 90  |     |     |     |     | 95  |     |
| Asn | Met | Thr | Val | Ser | Ser | Ala | Ala | Ala | Ala | Glu | Asn | Met | Phe | Thr | Gln |
|     |     |     |     | 100 |     |     |     |     | 105 |     |     |     |     | 110 |     |
| Met | Gly | Leu | Asp | Thr | Arg | Pro | Ser | Met | Lys | Glu | Ala | Gly | Gly | Lys | Glu |
|     |     |     | 115 |     |     |     |     | 120 |     |     |     |     | 125 |     |     |
| Glu | Gly | Pro | Pro | Gln | Ala | Phe | Pro | Ile | Gln | Thr | Val | Asn | Gly | Val | Pro |
|     |     | 130 |     |     |     |     | 135 |     |     |     |     | 140 |     |     |     |
| Gln | Tyr | Val | Ala | Leu | Asp | Pro | Lys | Met | Val | Ser | Ile | Phe | Met | Glu | Lys |
| 145 |     |     |     |     | 150 |     |     |     |     | 155 |     |     |     |     | 160 |
| Ala | Arg | Glu | Gly | Leu | Gly | Gly | Glu | Glu | Val | Gln | Leu | Trp | Phe | Thr | Ala |
|     |     |     |     | 165 |     |     |     |     | 170 |     |     |     |     | 175 |     |
| Phe | Ser | Ala | Asn | Leu | Thr | Pro | Thr | Asp | Met | Ala | Thr | Leu | Ile | Met | Ala |
|     |     |     | 180 |     |     |     |     | 185 |     |     |     |     | 190 |     |     |
| Ala | Pro | Gly | Cys | Ala | Ala | Asp | Lys | Glu | Ile | Leu | Asp | Glu | Ser | Leu | Lys |
|     |     | 195 |     |     |     |     | 200 |     |     |     |     | 205 |     |     |     |
| Gln | Leu | Thr | Ala | Gly | Tyr | Asp | Arg | Thr | His | Pro | Pro | Asp | Ala | Pro | Arg |
|     | 210 |     |     |     |     | 215 |     |     |     |     | 220 |     |     |     |     |

| | | | | | | | | | | | | | | |
|---|---|---|---|---|---|---|---|---|---|---|---|---|---|---|
| Pro<br>225 | Leu | Pro | Tyr | Phe | Thr<br>230 | Ala | Ala | Glu | Ile | Met<br>235 | Gly | Ile | Gly | Phe | Thr<br>240 |
| Gln | Glu | Gln | Gln | Ala<br>245 | Glu | Ala | Arg | Phe | Ala<br>250 | Pro | Ala | Arg | Met | Gln<br>255 | Cys |
| Arg | Ala | Trp | Tyr<br>260 | Leu | Glu | Gly | Leu | Gly<br>265 | Lys | Leu | Gly | Ala | Ile<br>270 | Lys | Ala |
| Lys | Ser | Pro<br>275 | Arg | Ala | Val | Gln | Leu<br>280 | Arg | Gln | Gly | Ala | Lys<br>285 | Glu | Asp | Tyr |
| Ser | Ser<br>290 | Phe | Ile | Asp | Arg | Leu<br>295 | Phe | Ala | Gln | Ile | Asp<br>300 | Gln | Glu | Gln | Asn |
| Thr<br>305 | Ala | Glu | Val | Lys | Leu<br>310 | Tyr | Leu | Lys | Gln | Ser<br>315 | Leu | Ser | Met | Ala | Asn<br>320 |
| Ala | Asn | Ala | Glu | Cys<br>325 | Lys | Lys | Pro | Met | Thr<br>330 | His | Leu | Lys | Pro | Glu<br>335 | Ser |
| Thr | Leu | Glu | Glu<br>340 | Lys | Leu | Arg | Ala | Cys<br>345 | Gln | Glu | Ile | Gly | Ser<br>350 | Pro | Gly |
| Tyr | Lys | Met<br>355 | Gln | Leu | Leu | Ala | Glu<br>360 | Ala | Leu | Thr | Lys | Val<br>365 | Gln | Val | Val |
| Gln | Ser<br>370 | Lys | Gly | Ser | Gly | Pro<br>375 | Val | Cys | Phe | Asn | Cys<br>380 | Lys | Lys | Pro | Gly |
| His<br>385 | Leu | Ala | Arg | Gln | Cys<br>390 | Arg | Glu | Val | Arg | Lys<br>395 | Cys | Asn | Lys | Cys | Gly<br>400 |
| Lys | Pro | Gly | His | Val<br>405 | Ala | Ala | Lys | Cys | Trp<br>410 | Gln | Gly | Asn | Arg | Lys<br>415 | Asn |
| Ser | Gly | Asn | Trp<br>420 | Lys | Ala | Gly | Arg | Ala<br>425 | Ala | Ala | Pro | Val | Asn<br>430 | Gln | Val |
| Gln | Gln | Ala<br>435 | Val | Met | Pro | Ser | Ala<br>440 | Pro | Pro | Met | Glu | Glu<br>445 | Lys | Leu | Leu |
| Asp | Leu<br>450 | | | | | | | | | | | | | | |

( 2 ) INFORMATION FOR SEQ ID NO:8:

( i ) SEQUENCE CHARACTERISTICS:
        ( A ) LENGTH: 150 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..150

( x i ) SEQUENCE DESCRIPTION: SEQ ID NO:8:

| ATG | ATC | GTA | CAC | ATC | CCC | CTG | ATG | CTC | CCA | GAC | CAT | TAC | CCT | ATT | TTA | 48 |
|---|---|---|---|---|---|---|---|---|---|---|---|---|---|---|---|---|
| Met | Ile | Val | His | Ile<br>5 | Pro | Leu | Met | Leu | Pro<br>10 | Asp | His | Tyr | Pro | Ile<br>15 | Leu | |
| 1 | | | | | | | | | | | | | | | | |

| CTG | CAG | CAG | AAA | TTA | TGG | GTA | TTG | GAT | TTA | CTC | AAG | AAC | AAC | AAG | CAG | 96 |
|---|---|---|---|---|---|---|---|---|---|---|---|---|---|---|---|---|
| Leu | Gln | Gln | Lys<br>20 | Leu | Trp | Val | Leu | Asp<br>25 | Leu | Leu | Lys | Asn | Asn<br>30 | Lys | Gln | |

| AAG | CAA | GAT | TTG | CAC | CAG | CTA | GGA | TGC | AGT | GTA | GAG | CAT | GGT | ATC | TCG | 144 |
|---|---|---|---|---|---|---|---|---|---|---|---|---|---|---|---|---|
| Lys | Gln | Asp<br>35 | Leu | His | Gln | Leu | Gly<br>40 | Cys | Ser | Val | Glu | His<br>45 | Gly | Ile | Ser | |

| AGG | GAC | | | | | | | | | | | | | | | 150 |
|---|---|---|---|---|---|---|---|---|---|---|---|---|---|---|---|---|
| Arg | Asp<br>50 | | | | | | | | | | | | | | | |

( 2 ) INFORMATION FOR SEQ ID NO:9:

( i ) SEQUENCE CHARACTERISTICS:

( A ) LENGTH: 50 amino acids
( B ) TYPE: amino acid
( D ) TOPOLOGY: linear ( i i ) MOLECULE TYPE: protein ( x i ) SEQUENCE DESCRIPTION: SEQ ID NO:9:

```
Met Ile Val His Ile Pro Leu Met Leu Pro Asp His Tyr Pro Ile Leu
 1               5                  10                  15
Leu Gln Gln Lys Leu Trp Val Leu Asp Leu Leu Lys Asn Asn Lys Gln
                20                  25                  30
Lys Gln Asp Leu His Gln Leu Gly Cys Ser Val Glu His Gly Ile Ser
            35                  40                  45
Arg Asp
    50
```

FELINE IMMUNODEFICIENCY VIRUS ISOLATE NCSU₁

This invention was made with government support under Public Health Service grant CA-43676 from the National Cancer Institute. The government may have certain rights to this invention.

RELATED APPLICATIONS

This application is a continuation-in-part of application Ser. No. 07/752,424, filed 3 Sep. 1991, now abandoned the disclosure of which is incorporated by reference herein in its entirety.

FIELD OF THE INVENTION

This invention concerns a unique isolate of Feline Immunodeficiency Virus which is highly infectious in vivo and produces a rapid inversion of the $CD4^+$: $CD8^+$ receptor ratio in infected subjects.

BACKGROUND OF THE INVENTION

Feline immunodeficiency virus (FIV), a lentivirus of cats, is associated with feline acquired immunodeficiency syndrome (AIDS). See N. Pedersen et al., Science 235: 790 (1987). Disorders associated with FIV infection include chronic gingivitis/stomatitis, chronic upper respiratory infections, chronic enteritis, and recurrent ocular disease. See R. English et al., J. Am. Vet. Med. Assoc. 196: 1116 (1990); N. Pedersen et al., Vet. Immunol. Immunopathol. 21: 111 (1989); J. Yamamoto et al., J. Am. Vet. Med. Assoc. 194: 213 (1989). What is known to date of the pathogenesis of FIV infection suggests that it is a valuable animal model for human immunodeficiency virus-1 (HIV-1)-induced AIDS. HIV-1 and FIV belong to the lentivirus subfamily of retroviruses, have similar morphology, protein composition, and $Mg^{2+}$-dependency of their reverse transcriptases (RT). See N. Pedersen et al., Science 235: 790 (1987); N. Pedersen et al., Vet. Immunol. Immunopathol. 21: 111 (1989). They both display tropism for T lymphocytes and monocytes and are capable of inducing these cells to form syncytia. See D. Brunner and N. Pedersen, J. Virol. 63: 5483 (1989); M. Gardner and P. Luciw, FASEB Journal 3: 2593 (1989). HIV-1 displays a particular tropism for $CD4^+$ lymphocytes, which leads to their gradual depletion and an inversion of the $CD4^+$: $CD8^+$ ratio. See A. Dalgleish et al., Nature 312: 763 (1984). The pathogenesis of HIV-1 infection has been attributed to virus-induced reduction of $CD4^+$ lymphocyte numbers and functions, resulting in decreased immune responsiveness and subsequent severe secondary infections. See M. McChesney and M. Oldstone, Ad. Immunol. 45: 335 (1989).

Yamamoto et al. recently studied the early events in the pathogenesis of FIV in kittens. See J. Yamamoto et al., Am. J. Vet. Res. 49: 1246 (1988). These kittens developed an acute infection syndrome similar to that seen in HIV-1, including low grade fever and transient generalized lymphadenopathy. More recent studies by Ackley et al., J. Virol. 64: 5652 (1990), utilized monoclonal antibodies directed against feline $CD4^+$ and $CD8^+$ homologues and Pan T cells to analyze lymphocyte profiles in SPF cats experimentally infected with FIV. These authors reported that a significant inversion of the $CD4^+$: $CD8^+$ ratios occurred only in cats infected for 18 months or more. The inversion was associated with a decrease in absolute number of $CD4^+$ cells and an increase in $CD8^+$ cells.

We have recently utilized a panel of monoclonal antibodies specific for feline T cell subsets (M. Tompkins et al., Vet. Immunol. Immunopathol. 26: 305 (1990)) to analyze T cell numbers and profiles in cats naturally infected with FIV. See C. Novotney et al., AIDS 4: 1213 (1990). Similar to the observation of Ackley et al. supra, cats naturally infected with FIV have an inverted $CD4^+$: $CD8^+$ ratio characterized by a selective reduction in $CD4^+$ cells. The present invention arose from our continuing efforts to better understand the early events in FIV infections.

SUMMARY OF THE INVENTION

A first aspect of the present invention is isolated feline immunodeficiency virus (FIV) having the identifying characteristics of FIV isolate NCSU₁.

A second aspect of the present invention is a biologically pure culture of host cells containing a FIV having the identifying characteristics of FIV isolate NCSU₁.

A third aspect of the present invention is isolated DNA coding for (a) an FIV having the identifying characteristics of FIV isolate NCSU₁, or (b) an antigenic fragment of an FIV having the identifying characteristics of FIV isolate NCSU₁.

Various vaccine formulations containing active agents derived from the foregoing FIV virus, DNA encoding the virus, and DNA encoding antigenic fragments of the virus are also disclosed herein.

A further aspect of the present invention is a host cell containing the recombinant DNA sequence as given above and which expresses the encoded polypeptide or antigenic fragment thereof.

Also disclosed are immunodeficient mice containing feline tissue, which feline tissue is capable of infection with a feline immunodeficiency virus, with the FIV preferably (but not necessarily) being FIV isolate NCSU₁.

DETAILED DESCRIPTION OF THE INVENTION

Figure 1:
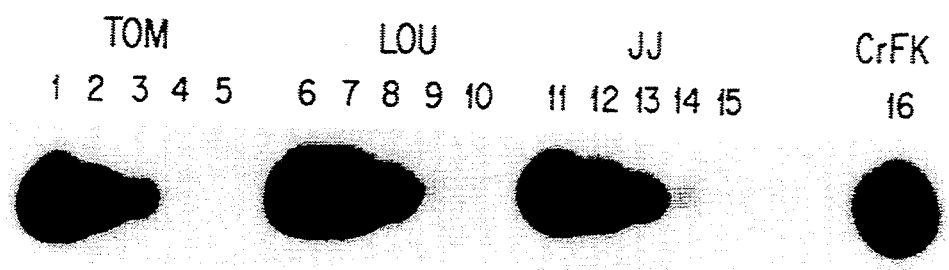
FIG. 1 shows hybridization analysis of PCR amplified FIV DNA from PBMC of NCSU₁ virus inoculum source cats. Lanes 1–15 represent serial 10 fold dilutions (beginning at $1 \times 10^6$ PBMC) from a naturally infected cat (TOM, lanes 1–5) and 2 SPF cats inoculated with PBMC from TOM (LOU, lanes 6–10; JJ, lanes 11–15). Lane 16 is PCR amplified control DNA from FIV-infected CrFK cells. TOM and JJ yielded provirus in as few as $1 \times 10^3$ PBMC and provirus was amplified in as few as $1 \times 10^2$ PBMC from LOU.

Amino acid sequences disclosed herein are presented in the amino to carboxy direction, from left to right. The amino and carboxy groups are not presented in the sequence. Nucleotide sequences are presented herein by single strand only, in the 5' to 3' direction, from left to right. Nucleotides and amino acids are represented herein in the manner recommended by the IUPAC-IUB Biochemical Nomenclature Commission, or (for amino acids) by three letter code in accordance with 37 C.F.R. §1.822 and established usage. See, e.g. PatentIn User Manual, 99–102 (November 1990) (U.S. Patent and Trademark Office, Office of the Assistant Commissioner for Patents, Washington D.C. 20231); U.S. Pat. No. 4,871,670 to Hudson et al. at Col. 3, lines 20–43 (applicants specifically intend that the disclosure of this and all patent references cited herein are to be incorporated herein by reference).

Aspects of the present invention are achieved by a virus having the identifying characteristics of the deposit designated Feline Immunodeficiency Virus (FIV-$NCSU_1$), made in accordance with the provisions of the Budapest Treaty on Jul. 23, 1991, with the American Type Culture Collection, 12301 Parklawn Drive, Rockville, Md. 20852 USA, and assigned ATCC Number VR2333.

A. Identification of Antigenic Fragments

Antigenic fragments of the present invention are peptides which contain at least one epitope (antibody binding site) which binds antibodies which bind to the FIV isolate of the present invention. The antigenic fragments are preferably capable of inducing an immune response when administered to a feline subject, as discussed in greater detail below. In addition, the antigenic fragments preferably bind antibodies which do not bind to prior FIV isolates. DNA encoding such antigenic fragments may be used to transform host cells to thereby produce such antigenic fragments, as explained in greater detail below.

Antigenic fragments may be identified by a variety of means. A protein from FIV isolate $NCSU_1$, such as the envelope protein, may be fragmented with a protease, and the fragments tested to determine whether or not various ones react with antiserum against the protein. See, e.g., J. Robinson et al., *Mol. Cell Biochem.* 21, 23–32 (1978). Another technique is to synthesize peptides which are fragments of the entire protein, and determine whether the individual fragments are recognized by neutralizing antibodies against the protein. See, e.g., J. Gerin et al., in *Vaccines 85: Molecular and Chemical Basis of Resistance to Parasitic, Bacterial and Viral Diseases,* 235–239 (Lerner et al., eds. 1985). Still another method useful for obtaining immunogenic fragments of a protein is by isolation and identification of monoclonal escape mutants. In this strategy, FIV is produced in the presence of a monoclonal antibody to the virus. The only virus which can grow under these conditions are those with a mutation in the nucleotide sequence which codes for an epitope to which the monoclonal antibody binds. A mutant virus which grows under these conditions is referred to as the "monoclonal escape mutant." The monoclonal escape mutant is then sequenced and the mutant sequence compared with the nucleotide sequence of FIV isolate $NCSU_1$ to find the specific location of the mutation. The mutation is located in a region which codes for a protective epitope, or an "immunogenic fragment." See, e.g., J. Lopez et al., Location of a Highly Conserved Neutralizing Epitope in the F Glycoprotein of Human Respiratory Syncytial Virus, *J. Virol.* 64, 927 (1990).

B. Genetic Engineering Techniques

The production of DNA, vectors, transformed host cells, FIV virus, proteins, and protein fragments of the present invention by genetic engineering techniques can be carried out in accordance with methods known in the art. See, e.g., U.S. Pat. No. 4,761,371 to Bell et al. at Col. 6 line 3 to Col. 9 line 65; U.S. Pat. No. 4,877,729 to Clark et al. at Col. 4 line 38 to Col. 7 line 6; U.S. Pat. No. 4,912,038 to Schilling at Col. 3 line 26 to Col. 14 line 12; and U.S. Pat. No. 4,879,224 to Wallner at Col. 6 line 8 to Col. 8 line 59.

Vectors are replicable DNA constructs used to either amplify or express DNA of the present invention. An expression vector is a replicable DNA construct in which DNA of the present invention is operably linked to control sequences capable of expressing that DNA in a suitable host. Generally, control sequences include a transcriptional promoter, an optional operator sequence to control transcription, a sequence encoding suitable mRNA ribosomal binding sites, and sequences which control the termination of transcription and translation. Suitable vectors include plasmids, viruses (e.g., vaccinia virus, adenovirus, baculovirus, cytomegalovirus), phage, and integratable DNA fragments (i.e., fragments integratable into the host genome by recombination).

DNA regions are operably linked or operably associated when they are functionally related to each other. For example, a promoter is operably linked to a coding sequence if it controls the transcription of the sequence; or a ribosome binding site is operably linked to a coding sequence if it is positioned so as to permit translation.

Transformed host cells are cells which have been transformed or transfected with vectors as described above. Transformed host cells ordinarily express the DNA of the present invention. Suitable host cells include prokaryote, yeast or higher eukaryotic cells such as mammalian cells and insect cells.

Prokaryote host cells include gram negative or gram positive organisms, for example *Escherichia coli* (*E. coli*) or Bacilli. Exemplary host cells are *E. coli* W3110 (ATCC 27,325), *E. coli* B, *E. coli* X1776 (ATCC 31,537), *E. coli* 294 (ATCC 31,446). A broad variety of suitable prokaryotic and microbial vectors are available. *E. coli* is typically transformed using pBR322. Promoters most commonly used in recombinant microbial expression vectors include the β-lactamase (penicillinase) and lactose promoter systems (Chang et al., *Nature* 275, 615

(1978); and Goeddel et al., *Nature* 281, 544 (1979)), a tryptophan (trp) promoter system (Goeddel et al., *Nucleic Acids Res.* 8, 4057 (1980) and EPO App. Publ. No. 36,776) and the tac promoter (H. De Boer et al., *Proc. Natl. Acad. Sci. USA* 80, 21 (1983)). The promoter and Shine-Dalgarno sequence are operably linked to the DNA of the invention, i.e., they are positioned so as to promote transcription of messenger RNA from the DNA.

Eukaryotic microbes such as yeast cultures may also be transformed with vectors of the present invention. see, e.g., U.S. Pat. No. 4,745,057. *Saccharomyces cerevisiae* is the most commonly used yeast, although other yeast may also be used. Yeast vectors may contain an origin of replication from the 2 micron yeast plasmid or an autonomously replicating sequence (ARS), a promoter, an axl oncogene, sequences for polyadenylation and transcription termination, and a selection gene. An exemplary plasmid is YRp7, (Stinchcomb et al., *Nature* 282, 39 (1979); Kingsman et al., *Gene* 7, 141 (1979); Tschemper et al., *Gene* 10, 157 (1980)). Suitable promoting sequences in yeast vectors include the promoters for metallothionein, 3-phosphoglycerate kinase (Hitzeman et al., *J. Biol. Chem.* 255, 2073 (1980) or other glycolytic enzymes (Hess et al., *J. Adv. Enzyme Reg.* 7, 149 (1968); and Holland et al., *Biochemistry* 17, 4900 (1978)).

Host cells such as insect cells (e.g., cultured *Spodoptera frugiperda* cells) and expression vectors such as the baculovirus expression vector (e.g., vectors derived from *Autographa californica* MNPV, *Trichoplusia ni* MNPV, *Rachiplusia ou* MNPV, or *Galleria ou* MNPV) may be employed in carrying out the present invention, as described in U.S. Pat. Nos. 4,745,051 and 4,879,236 to Smith et al. In general, a baculovirus expression vector comprises a baculovirus genome containing the gene to be expressed inserted into the polyhedrin gene at a position ranging from the polyhedrin transcriptional start signal to the ATG start site and under the transcriptional control of a baculovirus polyhedrin promoter.

Examples of useful mammalian host cell lines are VERO and HeLa cells, Chinese hamster ovary (CHO) cell lines, and WI138, BHK, COS-7, CV, and MDCK cell lines. The transcriptional and translational control sequences in expression vectors to be used in transforming vertebrate cells are often provided by viral sources. For example, commonly used promoters are derived from polyoma, Adenovirus 2, and Simian Virus 40 (SV40). See, e.g., U.S. Pat. No. 4,599,308. An origin of replication may be provided either by construction of the vector to include an exogenous origin, such as may be derived from SV40 or other viral (e.g. Polyoma, Adenovirus, VSV, or BPV) source, or may be provided by the host cell chromosomal replication mechanism. If the vector is integrated into the host cell chromosome, the latter is often sufficient. Rather than using vectors which contain viral origins of replication, one can transform mammalian cells by the method of cotransformation with a selectable marker and DNA of the present invention, as described in U.S. Pat. No. 4,399,216.

C. Vaccines and Vaccine Formulations

The present invention provides for a variety of different vaccines useful for protecting feline species against FIV. Examples include live attenuated FIV isolate $NCSU_1$ virus, fixed whole virus, host cells which express virus antigen on the surface thereof (with the cells optionally fixed), preparations of virus fragments, purified proteins, antigenic fragments of proteins, and antigenic peptides which are derivatives of the antigenic fragments (as discussed in detail below). These various compounds and mixtures are generically referred to herein as active agents.

Live attenuated FIV isolate $NCSU_1$ virus is made by serial passage of the virus in tissue culture or genetically altered by recombinant techniques, in accordance with known procedures. Fixed virus is made by contacting live virus (attenuated or unattenuated) to a suitable fixative, such as formalin.

Preparations of viral fragments are made by lysing host cells, such as *E. coli* cells, transformed with a vector encoding the FIV isolate of the present invention or a portion thereof. For example, the vector may encode an FIV isolate which produces hollow virus particles which are antigenic. The lysate may be used in crude form, partially purified, or a particular viral protein (or antigenic fragment thereof) such as the envelope protein purified to homogeneity, and used as an active agent for a vaccine against FIV.

Host cells such as yeast cells may be transformed with vectors of the present invention capable of expressing FIV proteins, or antigenic fragments thereof, on the surface of the host cells, and the transformed host cells used as an active vaccine agent per se or fixed (e.g., with formalin) and used as an active agent.

Antigenic peptides are selected from the group consisting of antigenic fragments of FIV isolate $NCSU_1$ proteins, such as the envelope protein, and the antigenic equivalents thereof (i.e., analogs or derivatives). Antigenic peptides may be chemically synthesized or produced by recombinant techniques. The antigenic fragments are preferably not more than 20 amino acid residues in length, and are more preferably not more than 10 amino acid residues in length. The antigenic equivalents are selected from the group consisting of: (a) modified peptides comprising the aforesaid antigenic fragments modified by the inclusion of one or more changes to the amino acid sequence thereof; and (b) longer peptides which incorporate the sequence of the aforesaid fragments or the aforesaid modified peptides and which have (i) up to four extra amino acid residues attached to the C-terminal end thereof, (ii) up to four extra amino acid residues attached to the N-terminal end thereof, or (iii) up to four extra amino acid residues attached to the C-terminal end thereof and up to four extra amino acid residues attached to the N-terminal end thereof.

The term "antigenic equivalents," as used herein, refers to proteins or peptides which bind to an antibody which binds to the protein or peptide with which equivalency is sought to be established. Antibodies which are used to select such antigenic equivalents are referred to as "selection antibodies" herein. Preferred selection antibodies are monoclonal antibodies which bind to FIV isolate $NCSU_1$, but not to prior isolates of FIV such as the Petaluma strain isolated by N. Pedersen.

One or more amino acids of an antigenic peptide sequence may be replaced by one or more other amino acids which does not affect the antigenicity of that sequence. Such changes can be guided by known similarities between amino acids in physical features such as charge density, hydrophobicity/hydrophilicity, size and configuration. For example, Thr may be replaced by Ser and vice versa, Asp may be Replaced by Glu and vice versa, and Leu may be replaced by Ile and vice versa.

Antigenic equivalents may be formed by modifying reactive groups within a natural sequence or modifying the N-terminal amino and/or C-terminal carboxyl group. Such equivalents include salts formed with acids and/or bases, particularly physiologically acceptable inorganic and organic acids and bases. Other equivalents include modified carboxyl and/or amino groups on the synthetic peptide to produce esters or amides, or amino acid protecting groups such as N-t-butoxycarbonyl. Preferred modifications are those which provide a more stable, active peptide which will be less prone to enzymatic degradation in vivo, For use as a vaccine, the active agents of the present invention may be administered to the subject by any suitable means. Exemplary are by intramuscular injection, by subcutaneous injection, by intravenous injection, by intraperitoneal injection, by oral injection, and by nasal spray.

The amount of active agent administered will depend upon factors such as route of administration, species, and the use of booster administrations. In general, a dosage of about 0.1 to about 100 $\mu$g per pound subject body weight may be used, more particularly about 1 $\mu$g per pound.

Vaccine formulations of the present invention comprise the active agent in a pharmaceutically acceptable carrier. The active agent is included in the carrier in an amount effective to protect the subject being treated. Pharmaceutically acceptable carriers are preferably liquid, particularly aqueous, carriers, such as sodium phosphate buffered saline. The vaccine formulation may be stored in a sterile glass container sealed with a rubber stopper through which liquids may be injected and formulations withdrawn by syringe.

Vaccine formulations of the present invention may optionally contain one or more adjuvants. Any suitable adjuvant can be used, exemplary being aluminum hydroxide, aluminum phosphate, plant and animal oils, synthetic polymers and the like, with the amount of adjuvant depending on the nature of the particular adjuvant employed. In addition, the vaccine formulations may also contain one or more stabilizer, exemplary being carbohydrates such as sorbitol, mannitol, starch, sucrose, dextrin, and glucose, proteins such as albumin or casein, and buffers such as alkaline metal phosphates and the like.

D. Infection of Cats with FIV Isolate $NCSU_1$

Cats infected with FIV Isolate $NCSU_1$ are useful as a model system for the study of AIDS. Cats used for this purpose are preferably specific pathogen-free (SPF) cats, which are commercially available from sources such as Charles River Laboratories and Berkshire Laboratories. Infected cats are preferably maintained as a single colony of two or more cats, all infected with FIV isolate $NCSU_1$. The colony may be maintained in a single room with each cat housed in an appropriate cage, in accordance with standard practices for the maintenance of animals. Typically, a colony will consist of twenty to thirty cats, but this quantity will vary. Preferably, all members of the colony are SPF cats (i.e., free of pathogens other than FIV isolate $NCSU_1$).

SPF cats may be infected with NCSU Isolate $NCSU_1$ by any suitable means, such as by intraperitoneal, intravenous, or subcutaneous injection with a solution containing FIV Isolate $NCSU_1$. The solution may be blood from a previously infected cat, a blood fraction containing peripheral blood mononuclear cells from a previously infected cat, a pharmaceutically acceptable carrier such as saline solution containing FIV Isolate $NCSU_1$, etc.

Cats infected with FIV isolate $NCSU_1$ are particularly useful as a model system for AIDS because of the rapid inversion of the CD4+:CD8+ ratio caused by this virus. When used as a model system, the cat or cats infected with FIV isolate $NCSU_1$ is subjected to a treatment, which treatment is a candidate for use in combating AIDS in human subjects, and the progress of the FIV infection cat or cats thereafter examined. A control group of FIV isolate $NCSU_1$ infected but untreated, or placebo treated, cats may be included for the purpose of comparison. A slowing in the progression of the disease in the cats indicates that the treatment may be useful for combating AIDS in humans. Typically, the candidate treatment will then be subjected to further screening procedures and toxicological testing to determine whether the treatment may be useful in treating humans afflicted with AIDS. The treatment to which the cats are subjected may be any treatment, such as the administration of candidate drugs (e.g., candidate antiretroviral compounds) or drug combinations, including small organic compounds (e.g., antiviral nucleosides such as AZT and DDI), peptides, or proteins, which may be administered orally or parenterally, or may involve treatments other than the administration of drugs such as a biological response modifier or a vaccine. The progress of the disease in the cats after treatment can be monitored by any suitable means, such as examination for inhibition of the deterioration of CD4+ cell levels, declines in the circulating levels of the FIV GAG protein which corresponds to the p24 protein of HIV-1, the weight of the cat and its general appearance, etc.

E. Immunodeficient Mice containing Feline Tissue

An advantage of using infected cats as a model for AIDS as described above is that the FIV virus is not infectious to humans. A disadvantage of this model is that cats are somewhat large animals. Alternate animal models are the SCID-hu mouse and the hu-PBL-SCID mouse infected with the human immunodeficiency virus type 1 (HIV-1). See, e.g., J. McCune et al., *Science* 241, 1632–39 (23 Sep. 1988); D. Mosier et al., *Nature* 335, 256–59 (15 Sep. 1988). An advantage of the SCID-hu mouse as an animal model is its small size, but a serious disadvantage is that it carries the human AIDS virus. Accordingly, there is a continuing need for small animal models of HIV-1 infection which do not employ a virus infectious to humans.

Disclosed herein is an immunodeficient mouse containing feline tissue, which feline tissue is capable of infection with feline immunodeficiency virus (FIV). The mouse is infected with FIV. Any isolate of FIV may be employed, with a preferred isolate being FIV isolate $NCSU_1$. Mice are infected with FIV and used as an animal model for human AIDS in essentially the same manner as cats as described above.

Any suitable immunodeficient mouse may be employed, such as SCID mice (e.g., the C.B.-17 scid/scid mouse) athymic mice such as the nude mouse, and mice which have been rendered immunodeficient by treatment with radiation. The mouse may be deficient in T lymphocytes function alone (e.g., athymic mice), but is preferably deficient in both T and B lymphocyte function.

The feline tissue which the immunodeficient mice contains preferably comprises one or more of the following: feline thymus tissue, feline lymph node tissue, feline liver cells, feline bone marrow cells, feline peripheral blood mononuclear cells such as peripheral blood lymphocytes and peripheral blood monocytes, and feline spleen cells. The feline tissue may be introduced into the mouse by any suitable means, such as intraperitoneal injection, intravenous injection, surgical implantation, and combinations thereof. Feline tissue may be introduced as organized tissues (e.g., thymus and lymph node) or as discrete cells. One example is an immunodeficient mouse having feline thymus tissue and/or lymph node tissue surgically implanted. Another example is an immunodeficient mouse into which peripheral blood mononuclear cells have been intraperitoneally injected.

F. Diagnostic Probes

The FIV isolate $NCSU_1$ nucleotide sequence can be used to generate hybridization probes which specifically bind to FIV isolate $NCSU_1$ genetic material, or the genetic material of FIV isolates having the identifying characteristics of FIV isolate $NCSU_1$, to determine the presence of such FIV in cats. The hybridization probe may be selected so that it does not bind to other known FIV isolates, such as the Petaluma strain. The hybridization probes may be cDNA fragments or oligonucleotides, and may be labelled with a detectable group as discussed hereinbelow. Pairs of probes which will serve as PCR primers for the axl oncogene or a portion thereof may be used in accordance with the process described in U.S. Pat. Nos. 4,683,202 and 4,683,195.

For example, an illustrative embodiment of the above probes comprises DNA sequences set forth in SEQ ID NO:6 or fragments thereof.

The term "labelled" is used herein to refer to the conjugating or covalent bonding of any suitable detectable group, including enzymes (e.g., horseradish peroxidase, β-glucuronidase, alkaline phosphatase, and β-D-galactosidase), fluorescent labels (e.g., fluorescein, luciferase), and radiolabels (e.g., $^{14}C$, $^{131}I$, $^{3}H$, $^{32}P$, and $^{35}S$) to the compound being labelled. Techniques for labelling various compounds, including proteins, peptides, and antibodies, are well known. See, e.g., Morrison, *Methods in Enzymology* 32b, 103 (1974); Syvanen et al., *J. Biol. Chem.* 284, 3762 (1973); Bolton and Hunter, *Biochem. J.* 133, 529 (1973).

G. DNA Sequence and Genome Organization

Isolated DNA from the $NCSU^1$ provirus may be used to generate hybridization probes, which may be used in diagnostic assays as discussed above. Isolated DNA capable of expressing antigenic proteins or antigenic fragments thereof may be used for producing such proteins, which are also useful in diagnostic assays.

An aspect of the present invention is oligonucleotide probes which selectively hybridize to DNA encoding a group antigen (gag) polypeptide (or an antigenic fragment thereof) of FIV $NCSU_1$ under stringent conditions, which probes do not bind to DNA encoding the group antigen (gag) polypeptide of the following known FIV strains under the same stringency conditions: FIV-Petaluma (U.S. Pat. No. 5,037,753); FIV-PPR (Phillips et al., *J. Virology,* 64, 4605 (1990)); FIV-TM1 and FIV-TM2 (Miyazawa et al., *Arch. Virology* 108, 59 (1989)); FIV-UT113 (Verschoor et al., *J. Cell. Biochem.*, Suppl. 14D, 143 (1990). Conditions which will permit other DNA coding for an FIV gag polypeptide to hybridize to the DNA of FIV $NCSU_1$ gag polypeptide can be determined in a routine manner. For example, hybridization may be carried out under conditions of reduced stringency or even stringent conditions (e.g., conditions represented by a wash stringency of 0.3M NaCl, 0.03M sodium citrate, and 0.1% SDS at 60° C. or even 70° C. to DNA encoding the gag polypeptide of FIV $NCSU_1$ disclosed herein in a standard in situ hybridization assay. See J. Sambrook et al., Molecular Cloning, A Laboratory Manual (2nd Ed. 1989)(Cold Spring Harbor Laboratory)).

In general, DNA which codes for FIV gag polypeptide or antigenic fragments thereof and which hybridizes to DNA encoding gag polypeptide (or antigenic fragments thereof) of FIV $NCSU_1$ disclosed herein will be at least 75% homologous, 80% homologous, or even 85% homologous or more with the DNA of the gag polypeptide (or antigenic fragments thereof) of FIV $NCSU_1$ disclosed herein. Further, DNA which codes for FIV gag polypeptide (or antigenic fragments thereof), or which codes for a gag polypeptide or antigenic fragment coded for by DNA which hybridizes to the DNA which codes for FIV $NCSU_1$ gag polypeptide or antigenic fragment thereof, but which differ in codon sequence from these due to the degeneracy of the genetic code, are also an aspect of this invention. The degeneracy of the genetic code, which allows different nucleic acid sequences to code for the same protein or peptide, is well known in the literature. See, e.g., U.S. Pat. No. 4,757,006 to Toole et al. at Col. 2, Table 1.

A particular embodiment of the foregoing also disclosed herein is isolated DNA encoding a group antigen (gag) polypeptide, or an antigenic fragment thereof, of FIV $NCSU_1$, where the DNA is: (a) isolated DNA encoding group antigen (gag) polypeptide, or an antigenic fragment thereof, of FIV $NCSU_1$, (b) isolated DNA which hybridizes to isolated DNA of (a) above under stringent conditions and which encodes a feline immunodeficiency virus group antigen (gag) polypeptide or antigenic fragment thereof at least 75% homologous to isolated DNA of (a) above; or (c) isolated DNA differing from the isolated DNAs of (a) and (b) above in nucleotide sequence due to the degeneracy of the genetic code, and which encodes a feline immunodeficiency virus group antigen (gag) polypeptide or antigenic fragment thereof encoded by the isolated DNAs of (a) and (b), above.

An illustrative embodiment of the foregoing DNA which codes for FIV gag polypeptide (or antigenic fragments thereof) is DNA according to SEQ ID NO:6 or a fragment thereof.

Also disclosed herein are recombinant DNA sequences comprising vector DNA and a DNA encoding a group antigen (gag) polypeptide, or an antigenic fragment thereof, of FIV $NCSU_1$ (as given above).

The FIV provirus includes the structural genes for group-specific antigens (gag gene), envelope proteins (env gene) and reverse transcriptase (pol gene), as well as several short open reading frames similar to those of other lentiviruses. Omsted et al., *Proc. Natl. Acad. Sci. USA*, 86, 2448 (1989); Olmsted et al., *Proc. Natl. Acad. Sci. USA,* 86, 8088 (1989). The gag gene of FIV has been reported to encode a polyprotein of about 450 amino acids, which is subjected to postranslational cleavage. Talbot et al., *Proc. Natl. Acad. Sci. USA,* 86, 5743 (1989); Phillips et al., *J. Virology,* 64, 4605 (1990). The gag gene and its predicted protein product has been reported to be highly conserved among isolates of FIV. Phillips et al., *J. Virology*, 64, 4605 (1990); Morikawa et al., *Virology*, 183, 288 (1991). FIV gag gene has been expressed in baculovirus vectors and assembled into virus-like particles. Morikawa et al., *Virology*, 183, 288 (1991).

Isolated and purified FIV NCSU$_1$ group antigen (gag) polypeptide or antigenic fragments thereof are also an aspect of the present invention. These polypeptides or fragments are coded for by: (a) isolated DNA which encodes group antigen (gag) polypeptide, or an antigenic fragment thereof, of FIV NCSU$_1$; (b) isolated DNA which hybridizes to isolated DNA of (a) above under stringent conditions and which encodes a FIV gag polypeptide or antigenic fragment thereof at least 75% homologous to isolated DNA of (a) above; or (c) isolated DNA differing from the isolated DNAs of (a) and (b) above in nucleotide sequence due to the degeneracy of the genetic code, and which encodes a FIV gag polypeptide or antigenic fragment thereof encoded by DNAs of (a) or (b), above. By antigenic polypeptide is meant a polypeptide which is able to raise (with the aid of an adjuvant if necessary) an antibody response in cats. The polypeptide may be a fragment or a polypeptide naturally occurring in FIV particles. The fragment may be from a naturally occurring polypeptide or produced by isolation or synthesis of a gene encoding a desired polypeptide and expression within an appropriate expression system.

An illustrative embodiment of the foregoing polypeptides is one having the amino acid sequence according to SEQ ID NO:7. Polypeptides of the present invention include proteins homologous to, and having essentially the same biological properties as, the polypeptide of SEQ ID NO:7.

The present invention is explained in greater detail in the non-limiting Examples set forth below.

EXAMPLE 1

Animal Subjects

Nine adult, 3 to 5 year old, female, random source cats were used for this study. These cats had been in the laboratory animal care facility for two years prior to this study and their CD4+: CD8+ ratios determined several times during this period. Prior to infection, all animals were negative for feline leukemia virus (FeLV) by ELISA (TechAmerica, Omaha, Nebr.) and FIV by Western blot using FIV antigen purified from CrFK cells chronically infected with FIV (obtained from Dr. John Black, American Biotech, Milton, Tenn.). The cats had been vaccinated for feline panleukopenia, herpes, and calici viruses 10 months prior to this study. Four adult (1 year) specific pathogen free (SPF) cats were also used in one control group.

EXAMPLE 2

Isolation and Production of NCSU 1

Our original source of virus was from a cat (TOM) naturally infected with FIV as diagnosed by Western blot. TOM was negative for FeLV by ELISA. Peripheral blood mononuclear cells (PBMC) from TOM were demonstrated to carry FIV by $Mg^{2+}$ dependent reverse transcriptase activity and by polymerase chain reaction (PCR) and Southern analysis using primers and probes to FIV LTR and gag sequences. Failure to generate $Mn^{2+}$ dependent RT activity suggested that this cat was not infected with feline leukemia virus (FeLV) or feline syncytia forming virus (FeSFV). The CD4+: CD8+ ratio of TOM has been consistently below the 5th percentile reported for normal random source and pet cats (0.57, determined from flow analysis of 39 adult random source and pet cats) and has ranged from 0.29 to 0.40 for over a year. See C. Novotney et al., *AIDS* 4: 1213 (1990). PBMC from TOM were inoculated into two adult SPF cats (JJ and LOU) to provide a larger pool of cells for inoculum. Both SPF cats seroconverted by 2 months post infection (p.i.). By 6 months p.i., both cats had CD4+: CD8+ ratios below 1 (JJ=0.55, LOU=0.71). All three cats have remained positive for FIV by PCR/Southern and RT for a period of 6 months prior to and throughout the study reported here. FIV from TOM has been passaged in cultured feline PBMC for over a period of 6 months. We will refer to this virus throughout this text as the NCSU$_1$ isolate.

The NCSU$_1$ isolate (or "NCSU-1") was deposited with the American Type Culture Collection, 12301 Parklawn Drive, Rockville, Md. 20852 USA, in accordance with the provisions of the Budapest Treaty, on Jul. 23, 1991, and has been assigned ATCC Number VR2333.

EXAMPLE 3

Inferion of subjects with NCSU$_1$

For infection of the cats in this study, peripheral blood was drawn from the three cats described above and the PBMC separated on a 43%/62% discontinuous Percoll gradient. See M. Tompkins et al., *Vet Immunol. Immunopathol.* 6=1 (1987). A fraction of the PBMC from each cat was set aside for PCR/Southern analysis and the remainder pooled, counted and incubated in culture for 48 hours with 10 nMPMA. After 48 hours the cells were washed, counted and $2 \times 10^6$ PBMC inoculated intravenously into each of 6 adult random source cats. FIV infection was determined by the presence of antibody to the gag proteins (p15 and p26) by Western blot. See, e.g., C. Novotney et al., supra. Four SPF cats obtained from Liberty Laboratories (Liberty Corner, N.J.) were inoculated with $2 \times 10^6$ PMA-treated normal feline PBMC as mock-infection controls and 3 random source cats were used as uninfected controls.

EXAMPLE 4

Seroconversion and Clinical Syndromes of Adult CmsInfeced with NCSU 1

Six random source adult cats were inoculated with pooled PBMC from three cats infected with the NCSU$_1$ isolate of FIV in the manner described in Example 4 above. The donor cats were all seropositive for FIV at the time of bleeding by Western blot analysis, and their PBMC carried a relatively high burden of provirus as demonstrated by limiting dilution PCR and Southern analysis (FIG. 1). Plasma was collected prior to and at various weeks p.i. and tested for antibodies to FIV by Western blot in accordance with known procedures. See, e.g., C. Novotney et al., supra. None of the cats demonstrated antibody to either of the FIV gag proteins, p15 and p26, prior to infection or 1 week p.i. By 2 weeks p.i., all 6 cats had developed antibody to either p15 or p26, and by 4 weeks p.i., and throughout the duration of the study, all 6 cats demonstrated antibody to both these proteins All 6 cats appeared clinically normal until 9 weeks p.i., when all the cats became depressed and lethargic. None of the cats, however, developed a fever, and only a mild lymphadenopathy was noted. By 15 weeks p.i., all cats appeared clinically normal and have remained so to date (9 months p.i.).

EXAMPLE 5

Co-Culture and Reverse Transcriptase Assay

The presence of FIV in the peripheral blood of cats infected as described in Example 4 was determined by reverse transcriptase (RT) assay of co-cultures in accordance with known procedures. See, e.g., C. Novotney et al., supra. Briefly, PBMC from infected and normal cats were separated on Percoll and incubated with 10 µg/ml Con A for 24 hours. Then 100 U/ml recombinant human IL-2 (Hoffman-LaRoche, Nutley, N.J.) was added to the cultures. After 48 hours, $1 \times 10^6$ test PBMC were added to $2 \times 10^6$ normal PBMC and co-culture supernatants collected for assay for $Mg^{2+}$-dependent RT activity at 3–4 day intervals for 6 weeks.

The assay for RT activity was performed as described previously, see C. Novotney et al., supra, and is a modification of the procedure of Goff et al., J. Virol. 38: 239 (1981). Ten µl of culture supernatant was added to 50 µl of an RT reaction mixture (0.5 µg/ml poly(A) oligo (dt) in 50 mM Tris [pH 7.8], 7.5 mM KCL, 2 mM dithiothreitol, 5 mM $MgCl_2$, 0.05% Nonidet P-40, and 0.5 µCi [$^{32}$P] dTTP [ICN Biomedicals, Costa Mesa, Calif.]). After 2 hours at 37° C. 10 µl was spotted onto DE81 ion-exchange paper, dried, washed, and activity counted on a scintillation counter. Supernatant from FIV-infected CrFk cells was used as a positive control and supernatant from the target normal PBMC cultured alone was used as a negative control. All samples were run in quadruplicate. Results were converted to RT units which were calculated from the mean of quadruplicate samples of peak RT activity selected from sequential assays taken at 3–4 day intervals for 6 weeks after initiation of co-culture. RT units were calculated as follows:

$$RT\ unit = \frac{Mean\ CPM\ of\ test\ supernatant - Mean\ CPM\ of\ negative\ control\ supernatant}{Mean\ CPM\ of\ negative\ control\ supernatant}$$

EXAMPLE 6

Analysis of PBMC for FIV DNA by PCR Gene Amplification and Southern Analysis For PCR quantification of cell-associated virus, 5 ml of blood from infected and control cats was collected in EDTA and separated on Percoll. Five ml of blood usually yielded about $1 \times 10^7$ PBMC. For limiting dilution PCR analysis, serial tenfold dilutions of PBMC, beginning with $1 \times 10^6$ and ending with $1 \times 10^2$, were made. Each dilution was brought to a constant cell number of $2 \times 10^6$ cells with PBMC from a cat previously determined as FIV negative by PCR analysis.

Genomic DNA was collected following incubation in 500 microliters digestion buffer (100 mM NaCl, 10 mM Tris Cl, pH8, 25 mM EDTA, pH 8, 0.5% sodium dodecyl sulfate and 0.2 mg/ml Proteinase K) at 50° C. for 18 hours. The DNA was purified by phenol extraction and ethanol precipitation, dried, and redissolved in 64 µl sterile distilled water.

Primers for the PCR reaction were selected from a published FIV sequence. See R. Olmsted et al., Molecular cloning of feline immunodeficiency virus, Proc. Natl. Acad. Sci. 86: 2448 (1989). A 334 base pair fragment was amplified from the LTR region using primer $U_{5\text{-}1}$ (GGATGAGTATTGGAACCCTGAA) (SEQ ID NO:1) and primer $U_{5\text{-}1}$ (GATTCCGAGACCT-CACAGGTAA) (SEQ ID NO:2). The PCR procedure was performed using the Gene Amp ™ DNA amplification kit purchased from Perkin Elmer Cetus according to standard protocol. The entire 64 microliter DNA sample was used as template for each amplification.

After amplification, 10 microliters of the reaction product were run on a 1% Agarose gel, transferred to a nylon membrane (Biotrans ™ membrane, ICN), and baked for 2 hours at 80° C. After prehybridization for 12 hours, the membrane was hybridized for 12 hours with an internally-located oligonucleotide probe (GGACTTTTGAGTTCTCCCTT) (SEQ ID NO:3) end-labeled on the 5' end with $^{32}$P-ATP (5' DNA Terminus Labeling System ™, BRL, Life Technologies, Inc.). The membrane was washed three times with $1 \times$ SSC/0.1% SDS at room temperature for 15 minutes each and exposed to Kodak X-OMAT ™ AR film between two intensifying screens (Fischer Biotech L Plus ™) at −70° C. The film was processed after 2 and 12 hour exposures.

EXAMPLE 7

Figure 2:
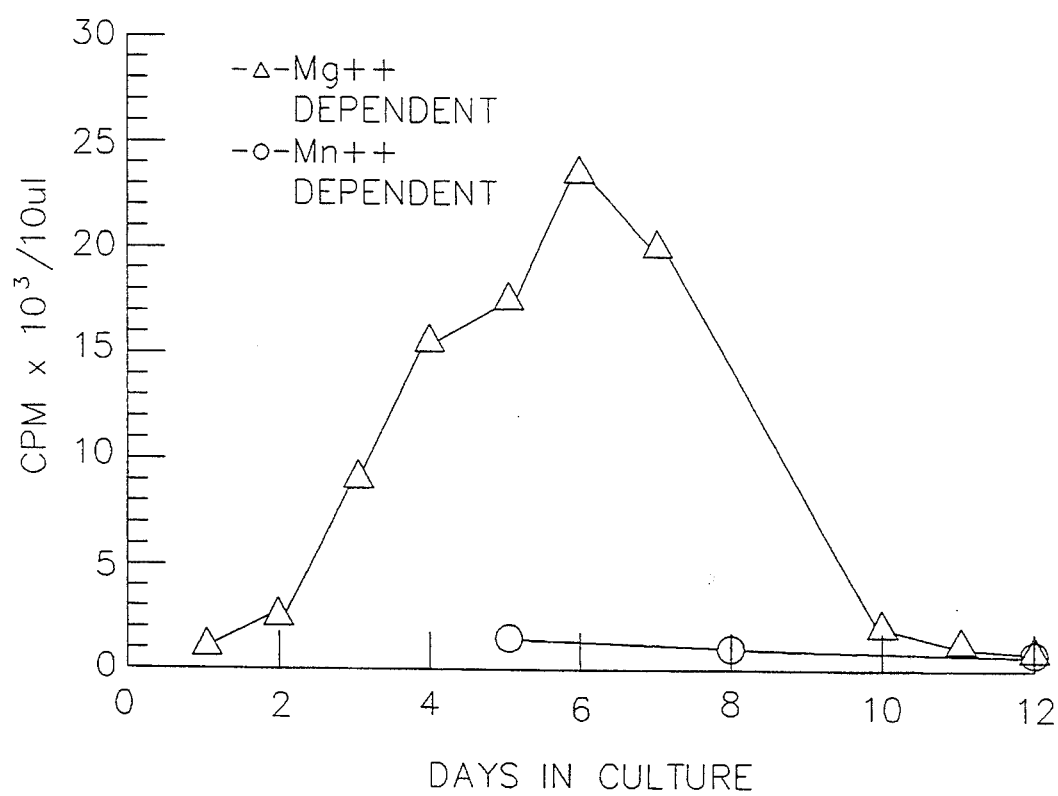
FIG. 2 shows $Mg^{2+}$- (FIV) and $Mn^{2+}$- (FeLV, FeSFV) dependent RT activity in co-culture supernatants of PBMC from a cat infected with FIV 6 weeks previously. Numbers represent the mean of quadruplicate samples.

Cell Associated Viremia as Measured by PCR/Southern Analysis and by RT Activity Both HIV-1 and FIV establish a cell associated viremia that can be demonstrated by co-culture and RT activity. See, e.g., M. McChesney and M. Oldstone, supra; N. Pedersen et al., Science 235:790 (1987). To determine how early after infection viremia was evident, lymphocytes from both the infected and uninfected cats were collected prior to and at 1, 2, 4, 6, and 9 weeks p.i., co-cultured with lymphocytes from normal cats, and the supernatants assayed for $Mg^{2+}$-dependent RT activity. Table 1 lists the RT activity for each cat at the various sampling times prior to and post infection. Although co-cultured for six weeks, PBMC from all cats were negative for RT activity prior to infection. By 4 weeks p.i., high RT activity, ranging from 35 to 77 RT units, was detectable in 5 of the 6 infected cats. The 6th cat (LIL) had low (7 RT units) but detectible activity. All 6 cats showed RT activity by 6 weeks pi. In contrast, RT activity was not detected in the culture fluid of the uninfected control cats (TRX, HIY, HOO). Although all cats tested negative for FeLV infection prior to infection with FIV, we tested them again for possible $Mn^{2+}$ dependent RT (indicative of FeLV and/or FeSFV infection) 6 weeks post FIV infection. All cats yielded high $Mg^{2+}$-dependent, but no $Mn^{2+}$-dependent RT activity. The results of one cat is shown in FIG. 2.

TABLE 1

REVERSE TRANSCRIPTASE ACTIVITY IN PBMC CO-CULTURES FROM FIV-INFECTED AND NORMAL CATS

| | | FIV Reverse Transcriptase Units[1] | | | | | |
|---|---|---|---|---|---|---|---|
| | | Weeks Post Infection | | | | | |
| Cat | Infection Status | 0 | 1 | 2 | 4 | 6 | 9 |
| TRX | Normal | 0.2 | 0.4 | 1.6 | 3.0 | 0.5 | 0.3 |
| HIY | Normal | 0.7 | 0.0 | 0.2 | 2.1 | 0.8 | 0.6 |
| HOO | Normal | 0.1 | 0.3 | 0.8 | 0.2 | 0.9 | 0.2 |
| PIX | Infected | 1.3 | 41.5 | 6.1 | 51.0 | 49.3 | 89.6 |
| MID | Infected | 0.2 | 1.5 | 7.1 | 39.0 | 46.4 | 87.8 |
| LIL | Infected | 0.2 | 1.0 | 9.0 | 7.3 | 23.2 | 49.1 |
| JIN | Infected | 0.1 | 0.3 | 5.0 | 34.8 | 13.1 | 8.1 |

TABLE 1-continued
REVERSE TRANSCRIPTASE ACTIVITY IN PBMC CO-CULTURES FROM FIV-INFECTED AND NORMAL CATS

| Cat | Infection Status | FIV Reverse Transcriptase Units[1] Weeks Post Infection | | | | | |
|---|---|---|---|---|---|---|---|
| | | 0 | 1 | 2 | 4 | 6 | 9 |
| HEA | Infected | 1.7 | 1.2 | 16.5 | 38.8 | 51.0 | 53.2 |
| BUT | Infected | 4.7 | 22.0 | 5.8 | 76.5 | 48.1 | 115.4 |

[1]RT units were calculated as given in Example 5 above.

At 4 weeks p.i., PBMC from 3 of the infected cats (PIX, MID, and LIL) and one control cat (TRX) were examined by PCR/Southern analysis for the presence of FIV provirus. All 3 infected cats were positive for FIV by PCR, while the normal cat was not. Thus although the PBMC from the cat LIL had very low RT activity at 4 weeks p.i. (7 units, Table 1), the PBMC were infected with FIV. All 6 infected cats were positive for FIV provirus at 4 months p.i. At 9 months (39 weeks) p.i., provirus was demonstrated by limiting dilution PCR/Southern analysis in as few as $10^2$–$10^3$ PBMC in all 6 cats (data not shown), indicating a heavy virus burden.

EXAMPLE 8

Lymphocyte Subset Analysis

One week prior to and at various times after infection, blood was collected for a complete blood count (CBC) and flow cytometric analysis (FACS) of lymphocyte subpopulations using a panel of monoclonal antibodies developed in our laboratory (M. Tompkins et al., *Vet. Immunol. Immunopathol.* 26: 305 (1990)). Cells were purified and prepared for flow analysis as previously described. C. Novotney et al., supra. Briefly, cells were purified over Histopaque (Sigma Chemical Company, St. Louis, Mo.), density 1.083 and incubated at a concentration of $5\times10^5$ cells in 100 $\mu$l of monoclonal antibody (1.572=Pan T; 3.357=CD8+; CAT3-0A=CD4+; $\alpha$Ig=B cell) overnight at 4° C. The cells were then washed 3 times and incubated for 30 minutes at 4° C. with a FITC-conjugated goat anti-mouse antibody that had been pre-absorbed with normal cat serum. The percent positively stained lymphocytes was determined by flow cytometric analysis using a Becton Dickinson FACScan. Absolute lymphocyte counts were performed on a Coulter counter by standard procedure.

EXAMPLE 9

Lymphocyte Subset Changes During Primary FIV Infection

Figure 3A:
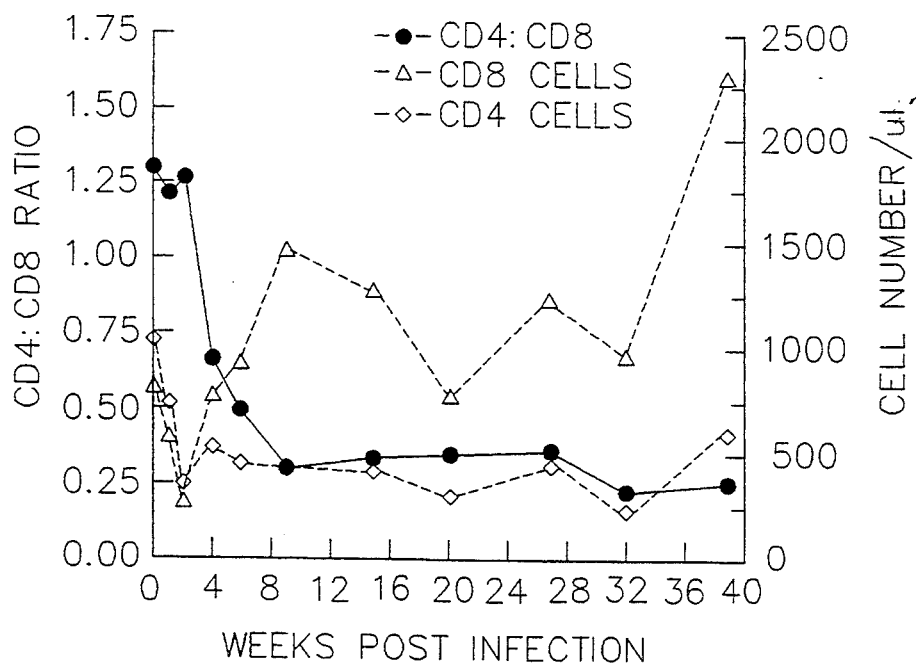
FIG. 3 shows changes in $CD4^+$ and $CD8^+$ cell numbers and the $CD4^+$: $CD8^+$ ratio during FIV infection. Cell numbers were determined by multiplying the percent positive $CD4^+$ or $CD8^+$ cells, determined by flow cytometric analysis, by the total lymphocyte count from a CBC (drawn at the same time as the sample for flow cytometry). (A) Cell numbers and ratio of a representative FIV-infected cat (MID). (B) Mean cell numbers and ratio of all 6 FIV-infected cats. There is a significant relationship between T cell numbers ($CD4^+$: $p=0.0005$; $CD8^+$: $p=0.0271$) and time post infection.

To examine lymphocyte profiles during the early stage of FIV infection, PBMC were collected prior to infection and at various weeks p.i. and analyzed by flow cytometry for the distribution of B cells, T cells, CD4+ T cells, and CD8+ T cells. Samples were collected at the same time from three uninfected random source adult cats to monitor any changes associated with frequent sample collection. FIG. 3A illustrates the CD4+ and CD8+ lymphocyte numbers and ratios of a representative cat (cat-MID). A lymphopenia developed at 2 weeks p.i. characterized by a profound decrease in both CD4+ and CD8+ lymphocyte populations. B cell numbers also decreased at this time (data not shown). The panlymphopenia was followed by a recovery of the CD8+ and B cell populations at 4 weeks p.i. The CD8+ cells continued to increase in number up to 9 weeks p.i., well beyond the preinfection level, where they leveled off and remained through the course of this study (39 weeks p.i.). In contrast, the CD4+ population showed only a small recovery at 4 weeks p.i. and remained low throughout the 39 week study period. This decrease in CD4+ cells and increase in CD8+ cells caused an early and prolonged inversion of the CD4+: CD8+ ratio in cat MID. All of the six infected cats showed a similar decrease in CD4+ numbers as cat MID. While all 6 cats demonstrated a recovery of CD8+ cells at 4 weeks and beyond, not all cats showed increases beyond preinfection levels.

Figure 3B:
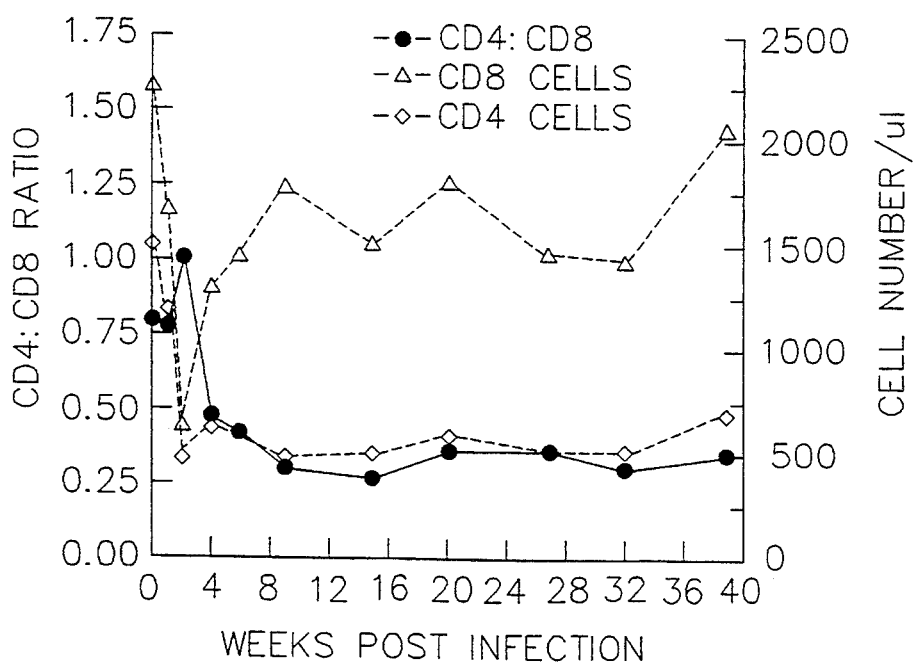
Figure 4:
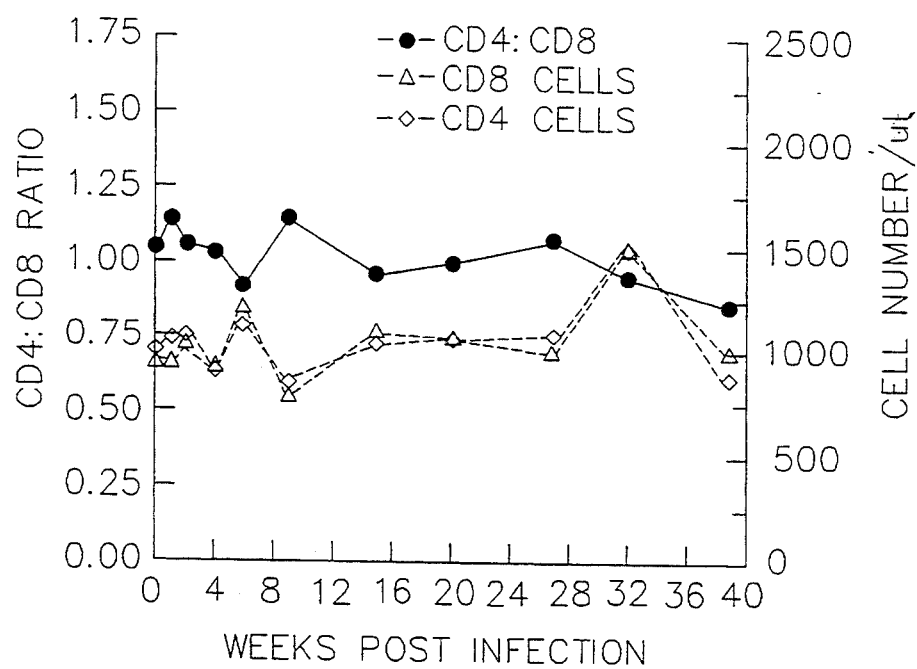
FIG. 4 shows the mean CD4+ and CD8+ cell numbers and CD4+: CD8+ ratio of 3 normal, random source cats that had blood samples collected at the same time as the infected cats. There is no significant relationship between T cell numbers and week of sampling.

The average CD4+ and CD8+ numbers and ratios for all six cats are shown in FIG. 3B. The pattern of response of the means of all 6 cats for CD4+ and CD8+ cell numbers and CD4+: CD8+ ratios is similar to the pattern shown by MID (FIG. 3A). After an initial lymphopenia, the CD8+ cell numbers increase while the CD4+ cell numbers do not, leading to a decline in the CD4+: CD8+ ratio. Statistical analysis of cell numbers regressed on time post infection demonstrated a significant relationship with time post infection for both CD4+ ($p=0.0005$) and CD8+ ($p=0.0271$) cells. In contrast, the CD4+ and CD8+ cell numbers in the uninfected controls remained steady throughout the study (FIG. 4) and were not significantly related to time p.i. Both cat populations developed a decreased number of circulating B cells during this study. Because this developed in the normal as well as the infected cats, it is likely related to repeat blood collection (data not shown).

Figure 5:
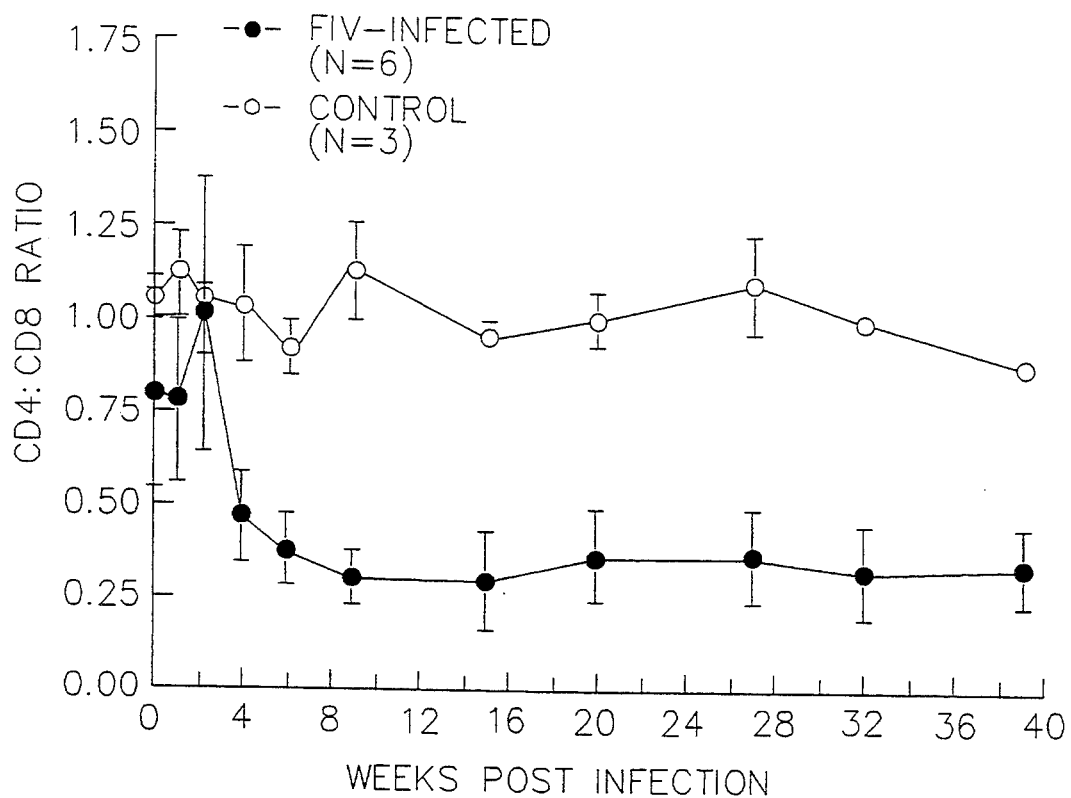
FIG. 5 shows the mean CD4+: CD8+ ratios of 6 FIV-infected cats and 3 control cats. The bars indicate 1 standard deviation. There is no significant difference in CD4+: CD8+ ratios of the two cat populations prior to infection (0 time), but at 4 weeks p.i. and there after, there is a significant difference in the ratios ($p<0.0001$).

The lymphocyte subset changes are dramatically illustrated by plotting the changes in the CD4+: CD8+ ratios of the FIV-infected cats. FIG. 5 compares the mean CD4+: CD8+ ratios of the control and FIV-infected cats. Although the mean CD4+: CD8+ ratio for the 6 cats prior to infection is below i ($0.80\pm0.26$) and slightly below that of the three control cats ($1.04\pm0.06$), the difference is not statistically significant, and the ratio is still within the normal range (0.57–1.81) determined from 39 adult random source cats. C. Novotney et al., *AIDS* 4:1213 (1990). The mean CD4+: CD8+ ratio of the infected cats declined to levels below the 5th percentile for random source cats (0.57) by 4 weeks p.i. Similar to cell numbers, there is a significant relationship between CD4+: CD8+ ratio and time p.i. for the FIV-infected cats ($p<0.0001$) but not the control cats. In addition, after 4 weeks p.i., there is a significant difference ($p<0.0001$) in mean CD4+: CD8+ ratios between the FIV-infected cats and the control cats (FIG. 5).

Figure 6:
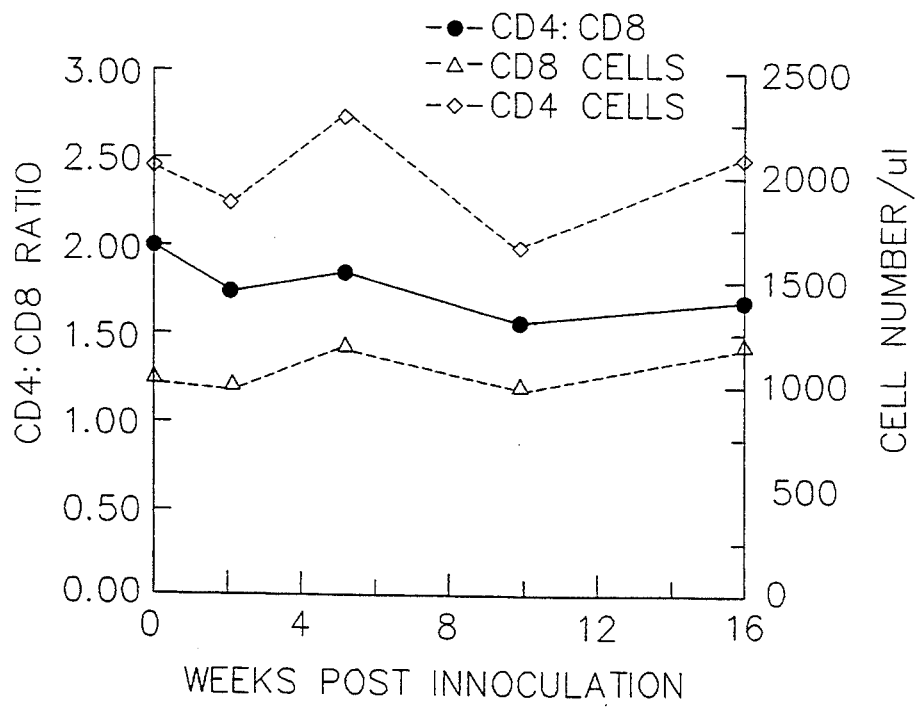
FIG. 6 shows the mean CD4+ and CD8+ cell numbers and CD4+: CD8+ ratio of 4 mock-infected cats. There is no significant relationship between the T cell numbers and week post inoculation.

To be sure that the cell changes seen in the FIV-infected cats were not a result of receiving foreign lymphocytes, 4 adult cats were inoculated with PMA-treated normal lymphocytes and their lymphocyte profiles examined at 2, 4, 10, and 16 weeks p.i. There were no changes in the lymphocyte distribution in any of the 4 cats as a result of inoculation with normal lymphocytes (FIG. 6). These results support the data suggesting that the lymphocyte changes seen in the FIV-infected cats are due to the virus infection.

In contrast to the studies reported herein, Pedersen et al., *J. Virol.* 64: 598 (1990), reported no significant difference between normal cats and cats experimentally infected with FIV for less than a year. However, cats infected for a year or more were beginning to show inverted CD4+: CD8+ ratios. Moreover, Ackley et al., *J. Virol.* 64: 5652 (1990), reported that experimental cats with FIV causes a reduction in the CD4+: CD8+ ratio only by 18 months or longer after infection. As was the case with some of the cats in our study, the CD4+: CD8+ inversion reported by Ackley et al. was due to a reduction in CD4+ numbers as well as an increase in CD8+ numbers. Our studies support those of Ackley et al. and suggest that FIV has a direct and profound effect on the immune system of the domestic cat.

We recently had the opportunity to compare our panel of monoclonal antibodies to feline lymphocyte subsets to those described and used by Ackley et al. (we thank Dr.'s C. Ackley and M. Cooper for providing their monoclonal antibodies for feline CD4 (Fel 7) and CD8 (FT2) markers for comparisons with our antibodies). We analyzed lymphocytes from both normal cats and cats infected with FIV, including the cats described herein, and found no differences in the percent positively staining cells with the two panels of antibodies.

EXAMPLE 10

Cloning of FIV Isole NCSU$_1$

Feline peripheral blood mononuclear cells infected with FIV Isolate NCSU$_1$ are obtained as described above and a genomic DNA library constructed therefrom in accordance with standard procedures. See W. Strauss, Preparation of Genomic DNA from Mammalian Tissue, in *Current Protocols in Molecular Biology*, pp. 2.2.1–2.2.3 (F. Ausubel, R. Brent, R. Kingston, D. Moore, J. Seidman, J. Smith, and K. Struhl, eds. 1989)(New York: Greene Publishing Associates and Wiley-Interscience). The purified genomic DNA is partially digested with Sau3A I (J. Weiss, in *Current Protocols In Molecular Biology*, supra pp. 5.3.4–5.3.8) and separated on a 0.5% low-melt agarose gel. DNA fragments with a molecular weight of 14–20 Kb are purified in accordance with known procedures (see J. Sambrook et al., *Molecular Cloning: A Laboratory Manual*, pp. 6.30–6.35 (2d Ed. 1989)(Cold Spring Harbor Laboratory Press)), ligated into EMBL-3 phage vector at the BAM HI cloning site, and packaged using the Packagene lambda gene packaging system.

Once the feline/NCSU$_1$ FIV provirus genomic DNA library is completed it is expressed and then screened for a full length genomic clone of the FIV provirus. Plaque lifts onto nitrocellulose membranes are screened via Southern hybridization with 5'LTR, 3'LTR, and GAG sequence specific DNA probes homologous to previous isolates of FIV to insure isolation of a full length clone.

The complete provirus clone is subcloned and purified for expression in feline host cells in accordance with either of two different procedures. In the first procedure, large quantities of proviral DNA are produced with the genomic clone, the DNA purified, and inserted into feline cells treated with calcium phosphate, DEAE-Dextran, or optionally with electroporation. see R. Kingston et al., in *Current Protocols in Molecular Biology*, supra, pp. 9.0.1–9.4.3. After transfection, the cells are treated to promote viral activity and thus produce an infectious clone. In the second method, the provirus from the EMBL-3 phage vector is cloned into a plasmid mammalian expression vector. A feline cell line is then transfected with the new provirus and vector, which provirus is then promoted with the expression vector's specific promoters.

EXAMPLE 11

Infection of SCID Mice with FIV

This example shows that when C.B.-17 scid/scid mice (SCID mice) are engrafted with sections of fetal feline thymus and/or lymph node, then given intraperitoneal injections of liver, bone marrow, peripheral blood lymphocytes, and/or spleen cells (SCID-fe mice), they are permissive for infection with feline immunodeficiency virus (FIV).

Fetal feline lymph node and thymus tissues are trimmed of fat and surgically implanted under the mammary fat pads of anesthetized C.B.-17 scid/scid mice. Immediately after implantation, each mouse is given a single intraperitoneal injection of a cell suspension comprised of finely minced feline liver, bone marrow, and spleen tissue, in physiological saline (approximately $10^8$ cells in approximately 100–200 $\mu$l of solution). The exact proportion of liver, bone marrow, and spleen tissue may vary depending upon availability.

Two weeks after implantation, 27 SCID-fe mice prepared in essentially the same manner as described above were injected intraperitoneally with $7 \times 10^6$ NCSU$_1$ FIV-infected feline peripheral blood mononuclear cells (PBMC) and 2 SCID-fe mice were given $3 \times 10^7$ uninfected feline PBMC. Ten of these mice were given a dose of 125 mg/kg/day Retrovir ® (azidothymidine, AZT) in the drinking water beginning 24 hours prior to virus challenge and continuing until the end of the study. Two weeks post-infection, the mice were sacrificed and implants were analyzed for FIV proviral DNA by PCR amplification of a 782 base pair segment of the gag open reading frame. Specificity was confirmed by hybridization to a radiolabeled internal oligonucleotide. The number of mice positive for FIV by PCR (summarized in Table 2 below) indicate a lower frequency of detection of FIV provirus in AZT-treated animals as compared to untreated.

TABLE 2

| Detection of FIV provirus in AZT-treated and Untreated Mice. | | | |
|---|---|---|---|
| | Untreated | AZT treated | Uninfected controls |
| Thymus implant | 11/17 (65%) | 2/10 (20%) | 0/2 (0%) |
| Lymph node implant | 11/17 (65%) | 4/10 (40%) | 0/2 (0%) |
| Both implants | 8/17 (47%) | 0/10 (0%) | 0/2 (0%) |

Hybridization intensities of FIV-positive samples in which equal amounts of DNA were amplified by PCR were compared to determine relative levels of provirus in each sample. Comparison of 5 untreated mice with 5 AZT-treated mice showed a significant reduction in provirus burden associated with AZT treatment. The stronger hybridization signal seen in the untreated animals suggests viral replication in the feline tissues. These data indicate that the FIV Infected SCID-fe mouse is a safe, realistic murine model for testing antiretroviral compounds.

EXAMPLE 12

Sequence of GAG gene of NCSU$_1$

The nucleotide sequence of the gag gene of NCSU$_1$ was determined in the following manner. Feline peripheral blood mononuclear cells infected with FIV Isolate NCSU$_1$ were obtained as described above (see Examples 3–6) and a genomic DNA library constructed therefrom in accordance with standard procedures. See W. Strauss, Preparation of Genomic DNA from Mammalian Tissue, In *Current Protocols in Molecular Biology*, pp. 2.21–2.23, F. Ausubel et al. (Eds.), New York: Greene Publishing Associates and Wiley-Interscience (1989). The gag gene of NCSU$_1$ was amplified by PCR using primers complementary to nucleotides 610–631 (SEQ ID NO:4) and 2026–2005 (SEQ ID NO:5) of FIV strain PPR (Phillips, et al., J. Virol. 64, 4605 (1990); GenBank accession no. m36968):

CTCTCTGAGA TGTCGTTGTA CC (SEQ. ID NO.:4)

TCTGGCCTCA TTTCTAATGA TG (SEQ. ID NO.:5)

The primers also contained restriction enzyme sites on the 5' ends to facilitate subcloning into appropriate plasmid vectors. Plasmid PSL 1190 (Pharmacia LKB Biotechnology, Piscataway, N.J.) was used, and the Xho I-BGL II site was used. See Brosius J. et al., *DNA*, 8, 759 (1989). Both strands of the cloned gag gene fragment of NCSU$_1$ were then sequenced by the dideoxynucleotide chain-termination method (Singer F, et al, *Proc. Natl. Acad. Sci. USA*, 74, 5463 (1977)) using Sequenase version 2.0 and T7 DNA polymerase (U.S. Biochemical, Cleveland, Ohio; used as described in manufacturer's instructions for double-stranded DNA). Computer analyses of the nucleotide and predicted amino acid sequences were performed with MacVector (International Biotechnologies Inc., New Haven, Conn.). Open reading frames (orfs) were identified by Fickett's method, which employs a TESTCODE algorithm and statistical parameters for predicting protein coding regions in DNA sequences. Fickett, *Nucl. Acids Res.* 10, 5303 (1982). Orfs defined by Fickett's method as having a coding probability above 0.92 were accepted as potential protein coding regions. Two orfs of 1350 and 150 base pairs were identified. The 1350 bp orf appeared to correspond to the gag orf by sequence comparisons to other FIV strains: FIV PPR; FIV-CG (GenBank accession number M25729); FIV-14 (GenBank accession number M25381); GenBank file FIV-Dixon; GenBank file FIV IMMDEF A; GenBank file FIV IMMDEF B; GenBank file FIV Z1; and GenBank file FIV GVEPX. The gag orf product is predicted to be 450 amino acids in length with a molecular mass of 49 kilodaltons. The predicted sites of gag polypeptide cleavage are before Pro-136 and after Leu-362, which results in gag polypeptides of 15, 25, and 10 kilodaltons. These predictions are the same as that observed for FIV strains Petaluma and PPR. Talbott et al., *Proc. Natl. Acad. Sci. USA*, 86, 5743 (1989); Phillips et al., *J. Virol.* 64, 4605 (1990). The nucleotide and predicted amino acid sequences for the NCSU$_1$ gag gene are shown in SEQ ID NO:6 and SEQ ID NO:7, respectively.

A 150 base pair orf (designated ORF 5) was found within the cloned gag gene fragment of NCSU$_1$, at nucleotide 663–812. This small orf is not present in reported DNA sequences of other FIV strains, as listed above. Four small orfs have been identified in the genome of FIV 14 and are located within the pol-env intergenic region, env, and sequence 3' to env (Olmsted et al., *Proc. Natl. Acad. Sci. USA*, 86, 8088 1989). Small orfs are a characteristic of other lentiviral genomes and are essential for the regulation of viral gene expression and replication. See Peterlin and Luciw, *AIDS*, 2, Suppl 1, S29 (1988).

The ORF 5 gene product is predicted to be 50 amino acids in length, have a molecular mass of 5.9 KDa and an isoelectric point of 7.32, be leucine rich (20%) and basic (18% lysine+histidine+arginine). Attempts to align the deduced amino acid sequence of ORF 5 with analogous sequences from other lentiviruses (HIV, SIV, visna virus, and equine infectious anemia virus) were unsuccessful. The nucleotide and deduced amino acid sequences of NCSU$_1$ ORF 5 are shown in SEQ ID NO:8 and SEQ ID NO:9, respectively. ORF 5 is one nucleotide out of frame with the gag orf.

The ORF 5 gene product is predicted to have a helix-turn-helix structural motif, spanning amino acids 18–41, which is found in some DNA-binding proteins. A potential RNA splice-acceptor site is located near the start of ORF 5, indicating that this orf may serve as an exon for a spliced transcript. This data suggests that the ORF 5 gene product functions in the regulation of viral gene expression or replication, and distinguished NCSU$_1$ from other FIV strains.

The foregoing examples are illustrative of the present invention, and are not to be construed as limiting thereof. The invention is defined by the following claims, with equivalents of the claims to be included therein.

That which is claimed is:

1. An isolated feline immunodeficiency virus (FIV) which is NCSU$_1$, having the assigned ATCC deposit number VR2333.

2. A biologically pure culture of host cells containing the feline immunodeficiency virus of claim 1.

* * * * *

UNITED STATES PATENT AND TRADEMARK OFFICE
CERTIFICATE OF CORRECTION

PATENT NO. : 5,413,927
DATED : May 9, 1995
INVENTOR(S) : Wayne A.F. Tompkins and Mary B. Tompkins It is certified that error appears in the above-identified patent and that said Letters Patent is hereby corrected as shown below:

Column 12, line 32, delete "6 = 1" and insert --16:1--.

Column 12, line 35, delete "10 nMPMA" and insert --10 nM PMA--.

Column 12, line 49, delete "Cms1nfeced" and insert --cats infected--.

Column 13, line 68, delete "$U_{5-1}$" and insert --$U_{3-1}$--.

Column 15, line 39, delete "5 x 105" and insert --5 x $10^5$--.

Column 16, line 39, delete "below i" and insert --below 1--.

Column 17, line 2, delete "experimental cats" and insert --experimental infection of SPF cats--.

Signed and Sealed this

Sixth Day of February, 1996

BRUCE LEHMAN

Commissioner of Patents and Trademarks